(12) United States Patent
Plessala et al.

(10) Patent No.: US 11,589,899 B2
(45) Date of Patent: Feb. 28, 2023

(54) ARTIFICIAL INSEMINATION SYSTEM AND METHOD OF USE

(71) Applicant: InnoMed One, LLC, Mobile, AL (US)

(72) Inventors: Kirby J. Plessala, Mobile, AL (US); Peter T. Falkner, Mobile, AL (US)

(73) Assignee: InnoMed One, LLC, Mobile, AL (US)

(*) Notice: Subject to any disclaimer, the term of this patent is extended or adjusted under 35 U.S.C. 154(b) by 783 days.

(21) Appl. No.: 16/535,506

(22) Filed: Aug. 8, 2019

(65) Prior Publication Data

US 2020/0022728 A1 Jan. 23, 2020

Related U.S. Application Data

(63) Continuation of application No. 16/349,159, filed as application No. PCT/US2017/064028 on Nov. 30, 2017, now Pat. No. 11,020,146, which is a continuation of application No. PCT/US2016/064243, filed on Nov. 30, 2016.
(Continued)

(51) Int. Cl.
*A61B 17/43* (2006.01)
*A61M 25/01* (2006.01)
*A61B 17/12* (2006.01)
*A61M 31/00* (2006.01)
(Continued)

(52) U.S. Cl.
CPC ............ *A61B 17/43* (2013.01); *A61M 25/01* (2013.01); *A61B 17/12159* (2013.01); *A61B 2017/4225* (2013.01); *A61F 6/146* (2013.01); *A61M 31/00* (2013.01)

(58) Field of Classification Search
CPC ......... A61B 17/28; A61B 17/04; A61B 17/11; A61B 17/12; A61B 17/42; A61B 17/4208; A61B 17/425; A61B 17/43; A61B 17/435; A61B 17/46; A61B 2017/1205; A61B 2017/2945; A61B 2017/301; A61B 2017/2904; A61B 2017/2905; A61B 2017/2926
See application file for complete search history.

(56) References Cited

U.S. PATENT DOCUMENTS 406,538 A * 7/1889 Rickolson ............... B25C 11/02
3,063,455 A * 11/1962 Markley ............ A61B 10/0291
606/119
(Continued)

*Primary Examiner* — Samuel G Gilbert
(74) *Attorney, Agent, or Firm* — Intellectual Property Consulting, LLC; Stephen M. Kepper

(57) ABSTRACT

The disclosed artificial insemination system comprises a cervical plug, catheter, and positioning tool. The cervical plug comprises a shield configured to cover an orifice, an arm attached to one side of the shield that is operable to be inserted into the cervical canal, and an insert member on the other side of the shield. A bore disposed within the cervical plug and extending through the insert member, shield, and arm is operable to receive the catheter used to deposit the semen sample. The positioning tool comprises a handle with a stem extending longitudinally therefrom and terminating at a bracket that is operable to receive the insert member and catheter and assist in preventing the cervical plug from becoming dislodged when the catheter is removed. A further object of this invention is the process by which the disclosed system is used to increase the efficacy of artificial insemination.

13 Claims, 12 Drawing Sheets

Related U.S. Application Data

(60) Provisional application No. 62/716,200, filed on Aug. 8, 2018.

(51) Int. Cl.
    *A61B 17/42*     (2006.01)
    *A61F 6/14*     (2006.01)

(56) References Cited

U.S. PATENT DOCUMENTS

| | | | | |
|---|---|---|---|---|
| 4,356,817 A | * | 11/1982 | McKibben | A61F 6/12 128/838 |
| 5,536,243 A | * | 7/1996 | Jeyendran | A61B 17/43 600/35 |
| 5,931,843 A | * | 8/1999 | Dunaway | A61B 17/326 606/118 |
| 2011/0152606 A1 | * | 6/2011 | Bollinger | A61B 17/43 600/35 |

* cited by examiner

ARTIFICIAL INSEMINATION SYSTEM AND METHOD OF USE

RELATED APPLICATIONS

This application claims priority to U.S. Provisional Application No. 62/716,200 filed Aug. 8, 2018 and is a continuation-in-part of U.S. application Ser. No. 16/349,159 filed May 10, 2019, which is the National Stage of International Application No. PCT/US2017/064028 filed Nov. 30, 2017 which claims priority to International Application No. PCT/US2016/064243 filed Nov. 30, 2016. The entire contents of the above applications are hereby incorporated by reference as though fully set forth herein.

BACKGROUND

Artificial insemination aims to place sperm into the reproductive system of a patient to promote pregnancy. Typically, artificial insemination is carried out when it is difficult or impossible for sperm to enter a patient's reproductive system during sexual intercourse. Intracervical insemination, where a semen sample is inserted into a patient's cervical canal, and intrauterine insemination, where a semen sample is inserted into a patient's uterine cavity, are the two most common artificial insemination procedures currently used. Generally, during such procedures, a patient's vaginal walls are held open by a medical device, such as a speculum. A semen sample is then inserted into the patient's cervical canal or uterine cavity, depending on which procedure is being performed, typically via a catheter-syringe assembly. After insertion, the semen is left to take by the patient's reproductive system.

However, a portion of the semen sample is often lost by leaking from the cervical canal into the vaginal cavity of the patient due to reflux caused by uterine contractions. Accordingly, unless a barrier is established between the patient's cervical canal and vaginal cavity after the semen sample is inserted, the efficacy of the insemination procedure may be diminished due to such reflux.

In order to prevent such reflux, a plug may be introduced at the cervical os. Such plugs vary in size and shape, but the general configuration consists of some form of wall or barrier, with a bore usually in the center of the barrier. The catheter is then fed through bore of the plug and inserted into the cervical canal or uterine cavity where a semen sample is directed through the catheter and deposited. After insemination, the catheter is then removed as any foreign object in the cervical canal or uterine cavity can trigger a biological response that may diminish the possibility of an egg being fertilized.

However, due to frictional forces between the interior surface of the bore within the plug and the exterior surface of the catheter, the plug may become somewhat dislodged or displaced when the catheter is removed, which diminishes the utility of the plug serving as a barrier. Accordingly, there is a need for a device and comprehensive artificial insemination system that holds the cervical plug in place while simultaneously allowing the catheter to be removed.

BRIEF SUMMARY OF INVENTION

The present invention seeks to meet these needs by providing an artificial insemination system comprising a cervical plug, catheter, and the needed positioning tool to hold the cervical plug in place while the catheter is removed from the patient's reproductive system. The cervical plug comprises a shield configured to cover an orifice, such as the cervical os of a patient, an arm that extends from one side of the shield and an insert member attached to the other side of the shield, wherein a bore extends longitudinally through the cervical plug and is operable to receive a catheter. The preferred embodiment for the cervical plug is disclosed in U.S. application Ser. No. 16/349,159, the contents of which are incorporated fully herein. The positioning tool comprises a handle with a stem extending longitudinally therefrom and terminating at a bracket, wherein the bracket further comprises a bottom segment attached to two opposing spaced apart segments extending in an upward direction therefrom. The bracket is operable to receive the insert member of the cervical plug to assist in holding the cervical plug in position at the cervical os while in use and while the catheter is removed.

Another aspect of this invention is a method utilizing the above described system to increase the efficacy of artificial insemination. The method comprises the steps of providing the above described cervical plug, catheter, and positioning tool followed sequentially by the following steps: inserting the catheter through the bore of the cervical plug; guiding the catheter and cervical plug through the vaginal canal until the shield covers and forms a seal around the cervical os; advancing the catheter into the uterus; introducing a semen sample into the uterine cavity. After the semen sample has been deposited, it becomes necessary to remove the catheter from the uterine cavity without dislodging the cervical plug. In order to accomplish this task, the method further comprises the step of introducing the positioning tool into the cervical canal and engaging the insert member of the plug with the bracket of the positioning tool; thereafter, the user applies gentle resistance to the cervical plug to counter the frictional forces created when the catheter is subsequently removed.

DETAILED DESCRIPTION

Figure 1:
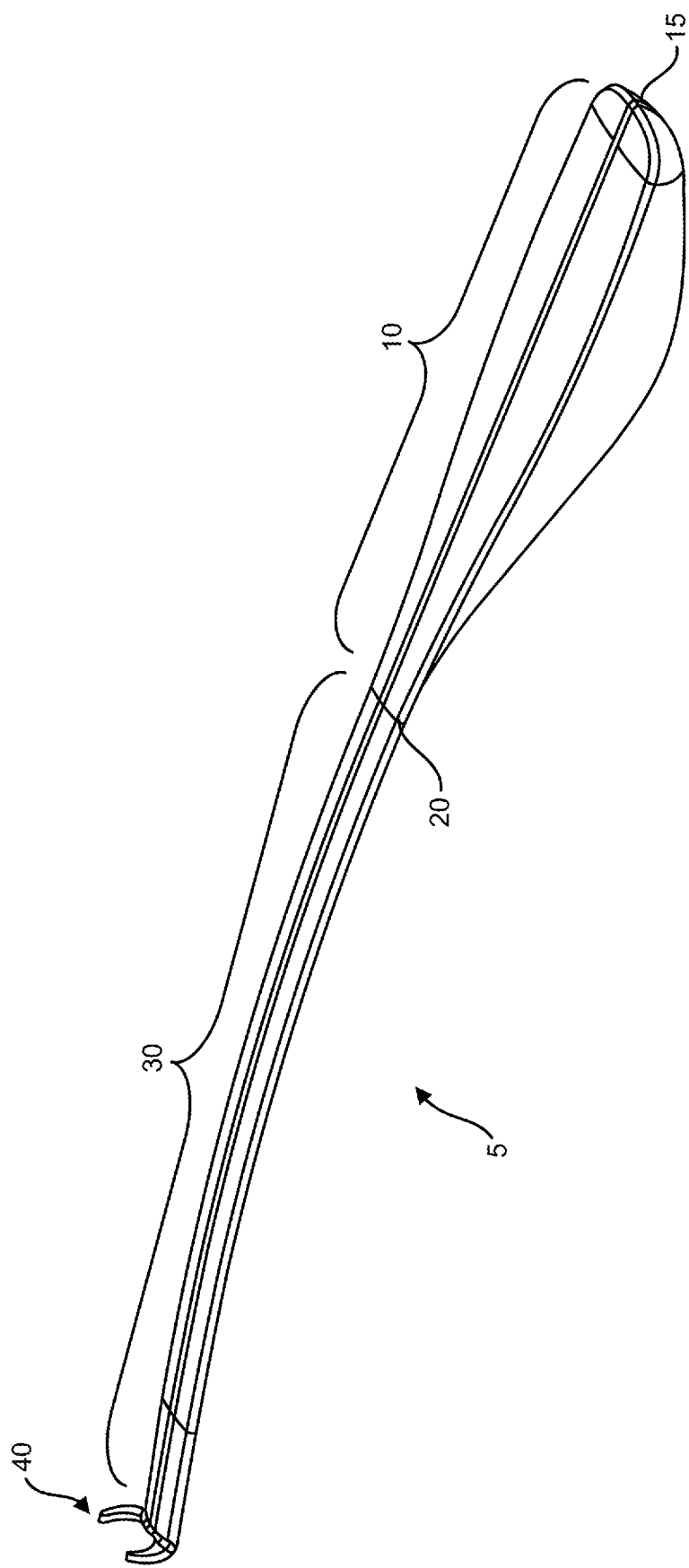
FIG. 1 is perspective view showing the positioning tool of the disclosed system.
Figure 2:
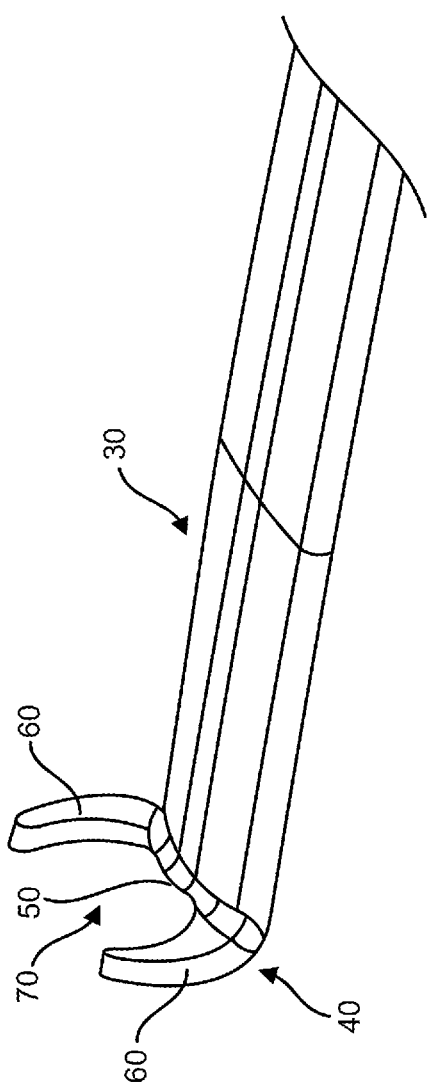
FIG. 2 is focused perspective view showing the distal end of the positioning tool of the disclosed system.

Turning to FIG. 1, a perspective view of the of the positioning tool 5 is shown. The tool 5 generally comprises a handle 10 on one end having a proximal end 15 and a distal end 20, a stem 30 extending longitudinally therefrom and connecting to a bracket 40 at the other end of the tool 5. It is anticipated that the stem 30 can be manipulated to be curved as shown in FIG. 1, or alternatively, may take on other alignments, including but not limited to, a linear alignment. It is envisioned that the positioning tool 5, including the handle 10, stem 30, and bracket 40 are made from a rigid or semi-rigid material (e.g. medical-grade silicone rubber, metal, plastic, glass); however, any part thereof or the entire tool 5 may be made from a flexible material to better assist in the guiding and placement of the tool 5 within the patient's reproductive system. Turning to FIG. 2, the bracket 40 structurally comprises a bottom segment 50 that extends a general horizontal direction with two opposing and spaced apart segments 60 that originate at the bottom segment 50 and extend in a general vertical direction therefrom such the interior of the bracket is accessible through the opening 70 between the opposing segments 60. For purposes of this invention, it is anticipated that the two opposing segments may be linear or curvilinear.

Figure 3:
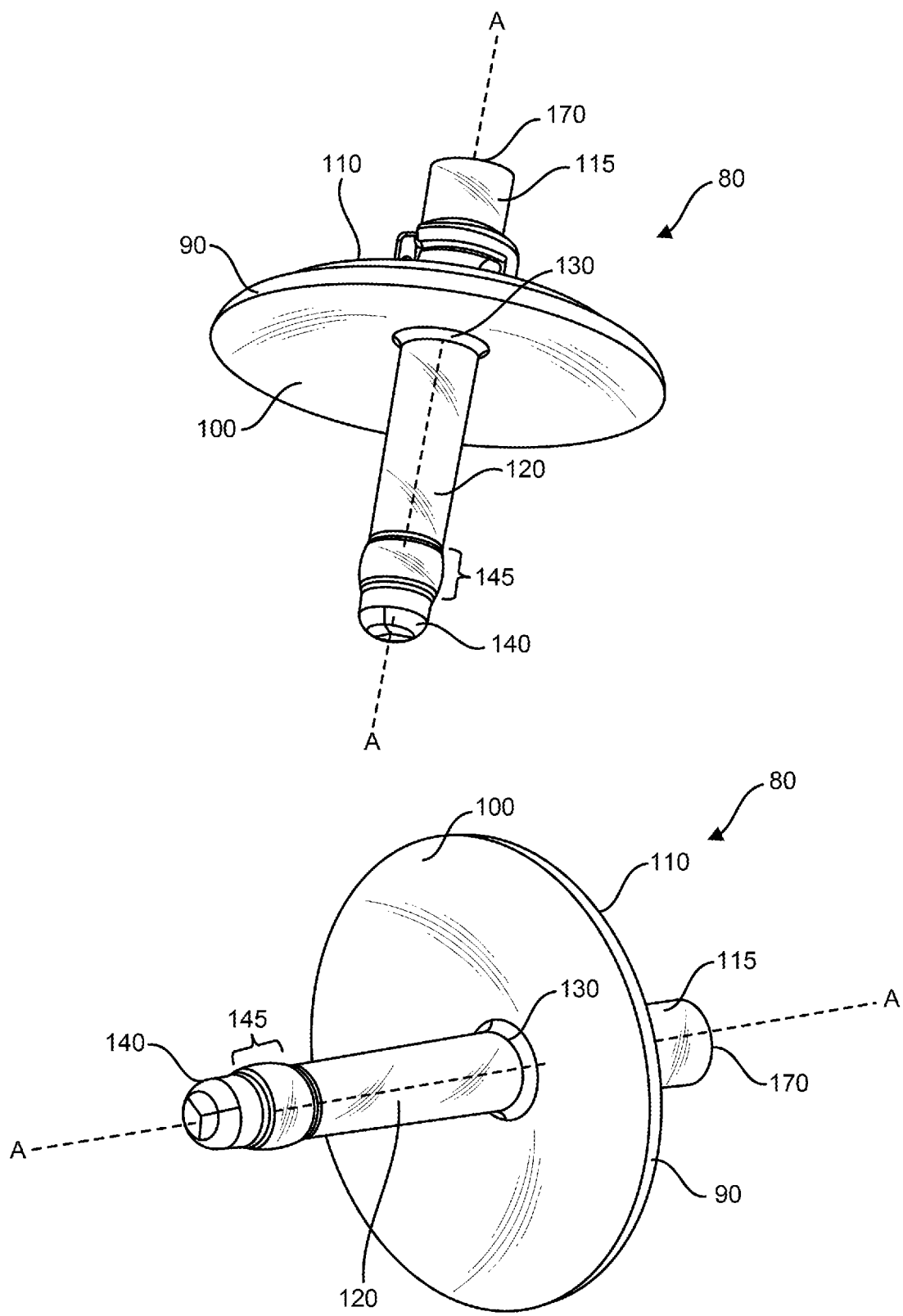
FIG. 3 includes multiple perspective views of the cervical plug of the disclosed system showing the valve in the closed position.
Figure 11:
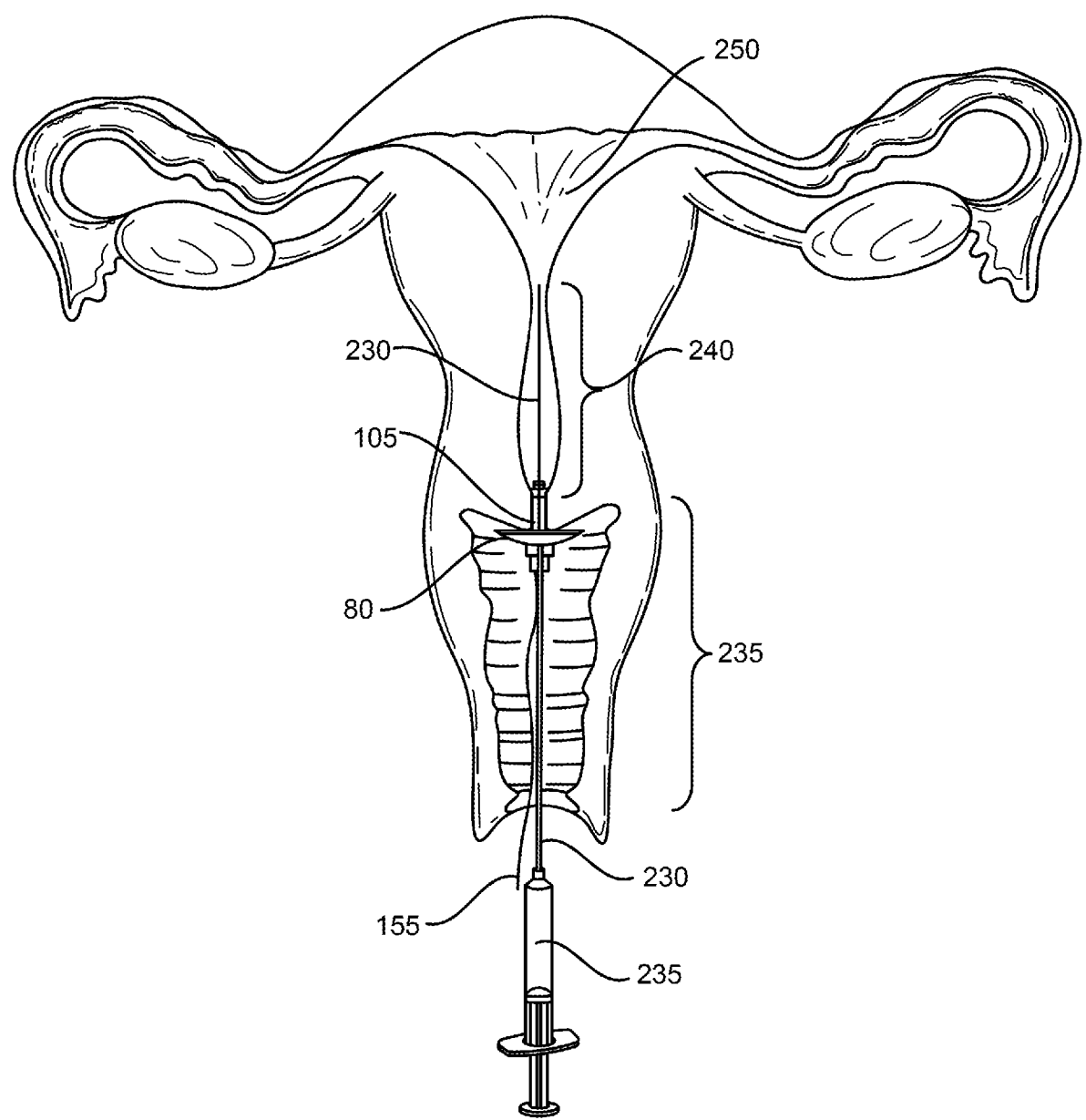
FIG. 11 is a perspective view of the disclosed system within a patient's reproductive system before the positioning tool is inserted.
Figure 12:
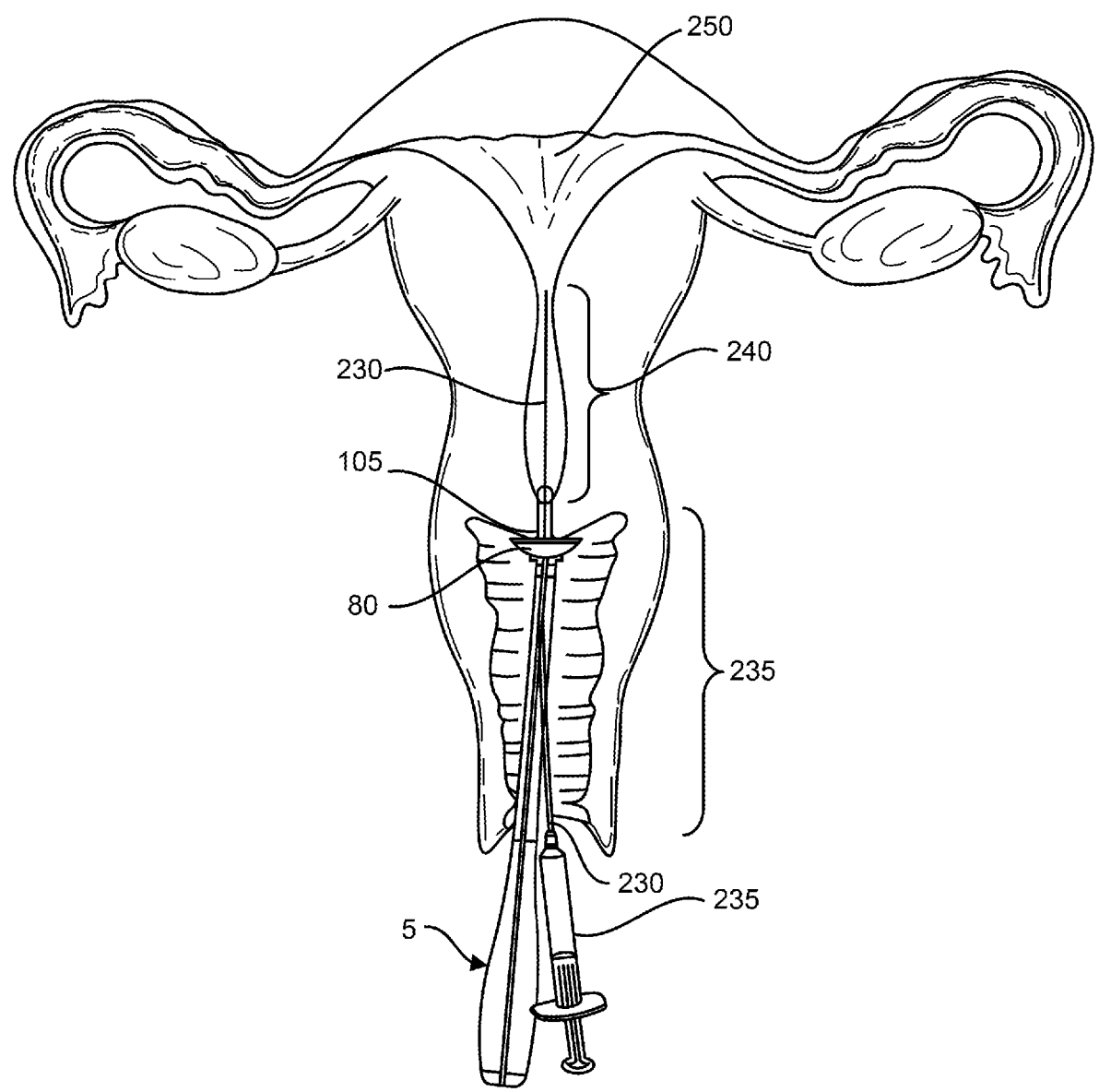
FIG. 12 is a perspective view of the disclosed system within a patient's reproductive system.

Turning to FIG. 3, the preferred embodiment for the cervical plug 80 is shown. The cervical plug 80 comprises a shield 90 having a first surface 100 and opposing second surface 110. As shown in the figure, the first surface 100 is preferably concave, but may be any shape to operably cover the cervical os 105 of a patient (as shown in FIGS. 11-12). Alternatively, the shield 90 may be of another shape suitable for covering the cervical os 105 of a patient, such as an elliptical shape. The shield 90 may be shaped and sized such that the shield 90 can cover the cervical os 105 of nulliparous, primiparous, or multiparous women. To minimize pain or discomfort experienced by a patient as the cervical plug 80 is inserted or removed from the patient's body, the shield 90 may be made of a material that is somewhat flexible such that the material may be deformed by pressure applied by a user of the device but return to its original shape when the pressure is removed. Alternatively, the shield 90 may be made of a material that is substantially rigid or semi-rigid. In addition, the shield 90 may be made of a material that is at least partially translucent or transparent, which may aid a user in inserting the device in the cervical canal.

Alternatively, the shield 90 may be made of an opaque material. The shield 90 may comprise medical-grade silicone rubber. Alternatively, the shield 90 may be made of any suitable material including, but not limited to, plastic, glass, ceramic, metal, any type of rubber, or any combination thereof.

The cervical plug 80 further comprises an arm 120 that attaches to the first surface 100 of the shield 90 at the arm's 120 proximal end 130; the distal end 140 of the arm 120 is operable to extend into the cervical os of a patient and may be conically shaped or substantially cylindrically shaped to ease discomfort caused by the insertion of the arm 120 into the patient. The arm 120 is sufficiently rigid for inserting the arm 120 into the cervical canal 240 of a patient (as shown in FIGS. 11-12), but the arm 120 may have some amount of flexibility in order to minimize pain or discomfort experienced by the patient as the cervical plug 80 is inserted or removed. Alternatively, the arm 120 may be made of a material that is substantially rigid. In addition, the arm 120 may be made of a material that is at least partially translucent or transparent. Alternatively, the arm 120 may be made of an opaque material. The arm 120 may comprise medical-grade silicone rubber. However, the arm may be made of any suitable material including, but not limited to, plastic, glass, ceramic, metal, any type of rubber, or any combination thereof.

The arm 120 may have a circumferential bulge 145 to help keep the cervical plug 80 in place with the arm 120 inserted into the cervical canal 240 during use. The bulge 145 is positioned along a length of the arm 120, preferably midway between the proximal end 130 and the distal end 140). Once the arm 120 is inserted into the cervical canal 240, as shown in FIGS. 11-12, the wider diameter of the circumferential bulge 145 provides resistance to removal of the arm 120 from the cervical canal 240, thereby helping to keep the cervical plug 80 in place for a period of time after semen has been introduced into the cervical canal 240 or uterine cavity 250 so that the plug 80 prevents leakage of semen from the cervical canal 240 into the vaginal canal 235. The bulge 145 preferably comprises a contoured surface to prevent discomfort, however, this patent envisions the bulge 145 having other similar configurations operable to prevent the cervical plug 80 from becoming dislodged.

The arm 120 may be permanently secured to the shield 90. For instance, the arm 120 and shield 90 may be molded as a unitary piece of material. Alternatively, the arm 120 may be secured to the shield 90 with an adhesive. A bore extends longitudinally through the center of the cervical plug 80 with one opening at the proximal end 170 of the insert member 115 and another opening at the distal end 140 of the arm 120; the bore is operable to receive a catheter along the directionally dashed line A through the cervical plug 80.

Figure 4:
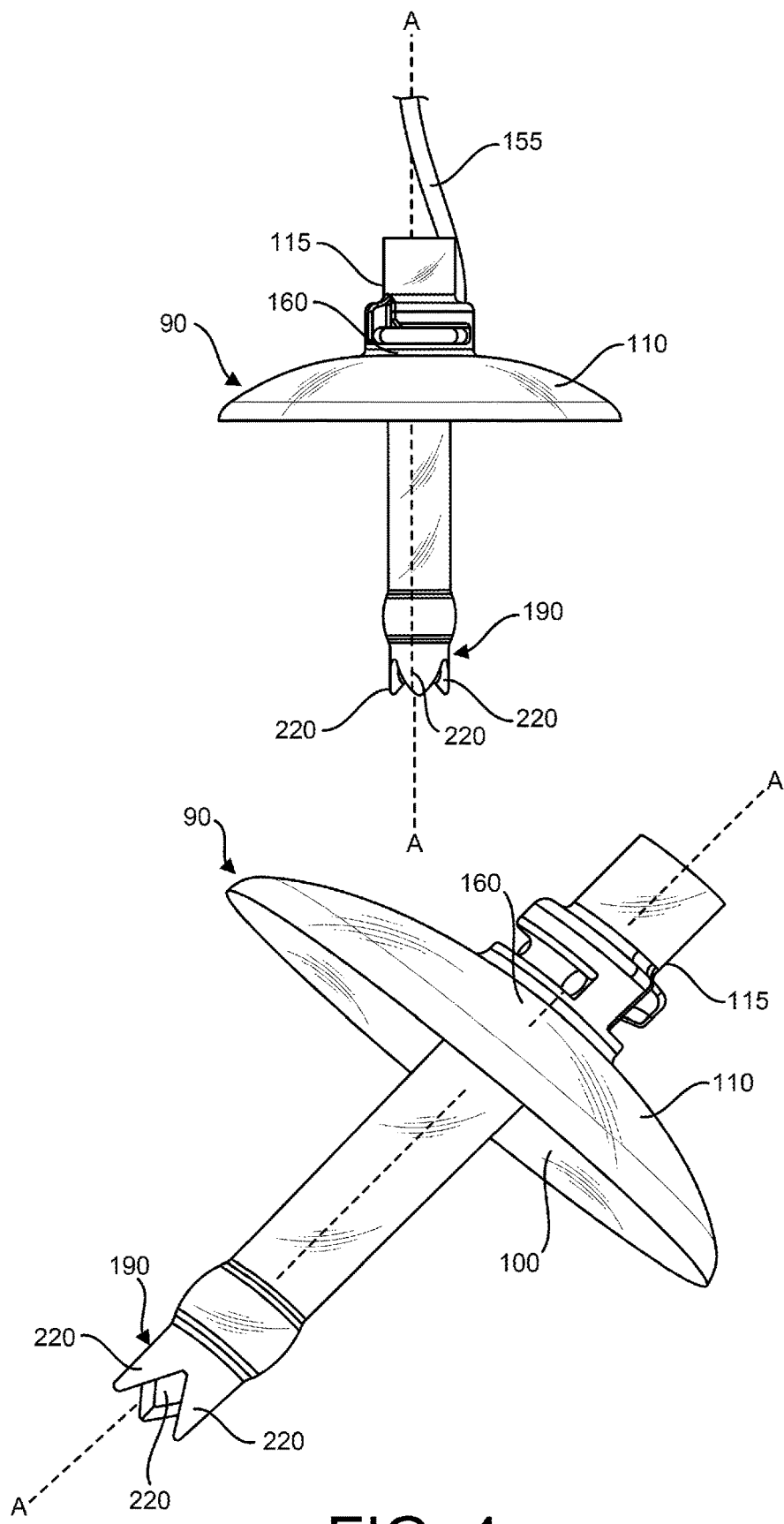
FIG. 4 includes alternative views of the cervical plug of the disclosed system with the valve in the open position.

Turning to FIGS. 3 and 4, the distal end 140 of the arm 120 is shown with an optional valve 190 that is operable between an open position (as shown in FIG. 4) and the closed position (as shown in FIG. 3). The valve 190 further comprises elastomeric flaps 220 integrally attached to the distal end 140 of the arm 120. These elastomeric flaps 220 are resiliently biased against each other when the valve is in the closed position (as shown in FIG. 3), such that they are operable to form a substantially fluid-tight seal over the opening at the distal end 140 of the arm 120.

The opposing second surface 110 of the shield 90 is attached to an insert member 115 at the distal end 160 of the insert member 115 and provides a protrusion. The insert member 115 may function as an aid for inserting and removing the cervical plug 80 from the cervical canal 240. The insert member 115 may be permanently secured to the shield 90. For instance, the cervical plug 80 may be molded as a unitary piece of material including the shield 90, arm 120, and insert member 115. Alternatively, the insert member 115 may be secured to the shield 90 with an adhesive. As illustrated in FIGS. 3-4, the insert member 115 may be secured to the shield 90 such that the insert member 115 forms a generally straight line with the arm 120. The insert member 115 may be made of a material that is at least partially translucent or transparent. Alternatively, the insert member 115 may be made of an opaque material. The insert member 115 may comprise medical-grade silicone rubber. Alternatively, the insert member 115 may be made of any suitable material including, but not limited to, plastic, glass, ceramic, metal, any type of rubber, or any combination thereof.

To facilitate removal of the cervical plug 80 after use, the insert member 115 may optionally have a string 155 attached thereto, as best seen in FIG. 4. The string 155 attaches to the cervical plug 80 via tying means through an annular cavity in the insert member 115, or alternatively, may be permanently affixed through molding means to the insert member 115. The string 155 may be a medical-grade suture, though any suitable material may be utilized. The string 155 may be of a sufficient length to extend through the vaginal canal 235 and outside of the patient's body when the cervical plug 80 is inserted in the cervical canal 230, as seen in FIG. 11-12. By pulling the string 155, the cervical plug 80 may be removed through the vaginal canal 235 without forceps or a similar device.

Figure 5:
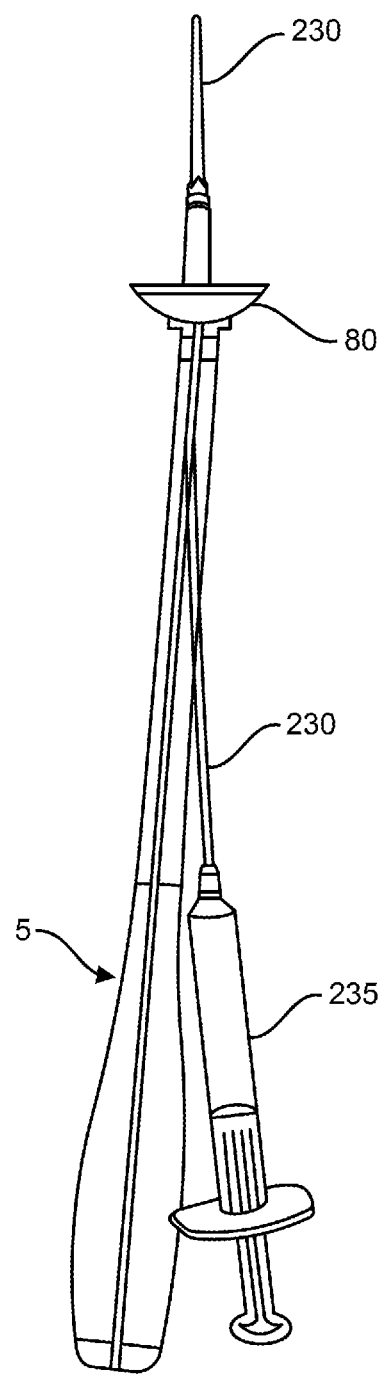
FIG. 5 is a top view of the disclosed system.
Figure 6:
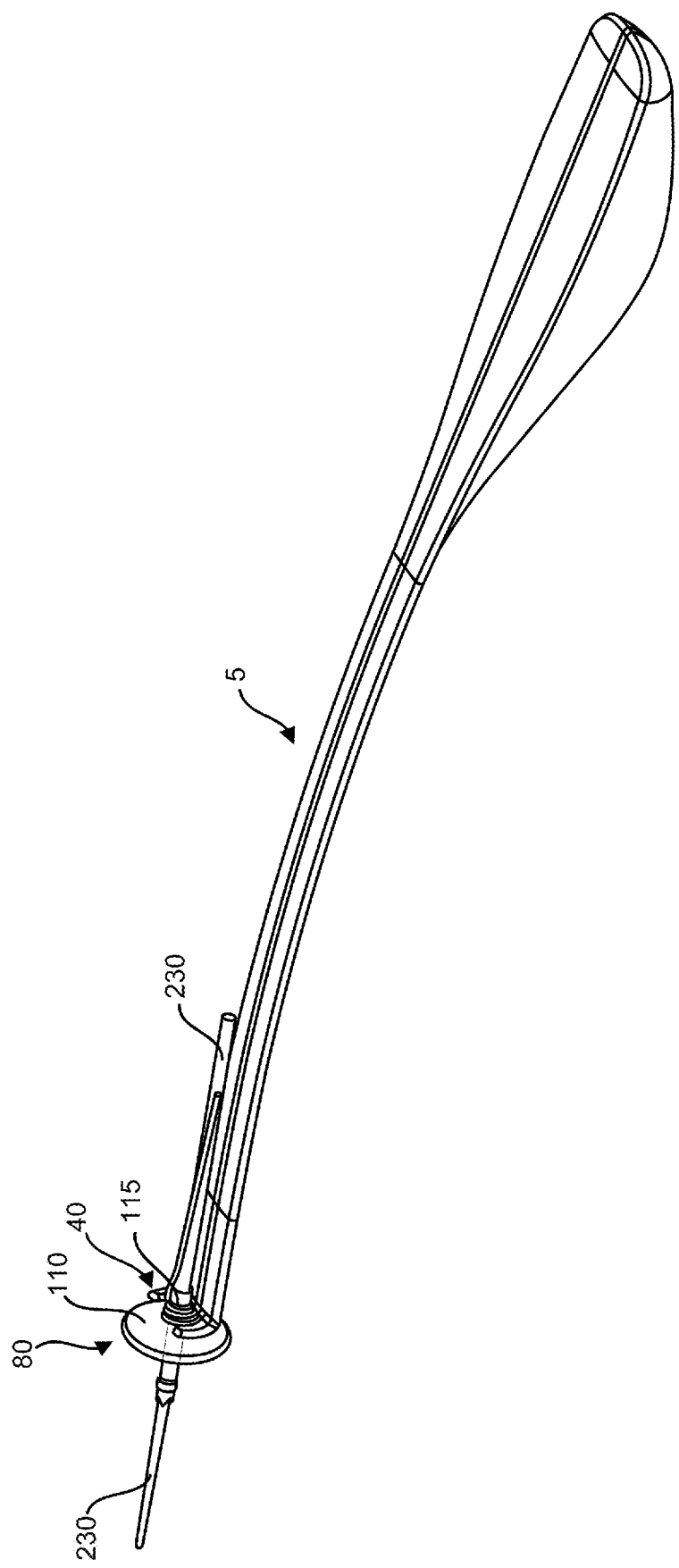
FIG. 6 is a perspective view of the disclosed system with the syringe removed from the catheter.
Figure 7:
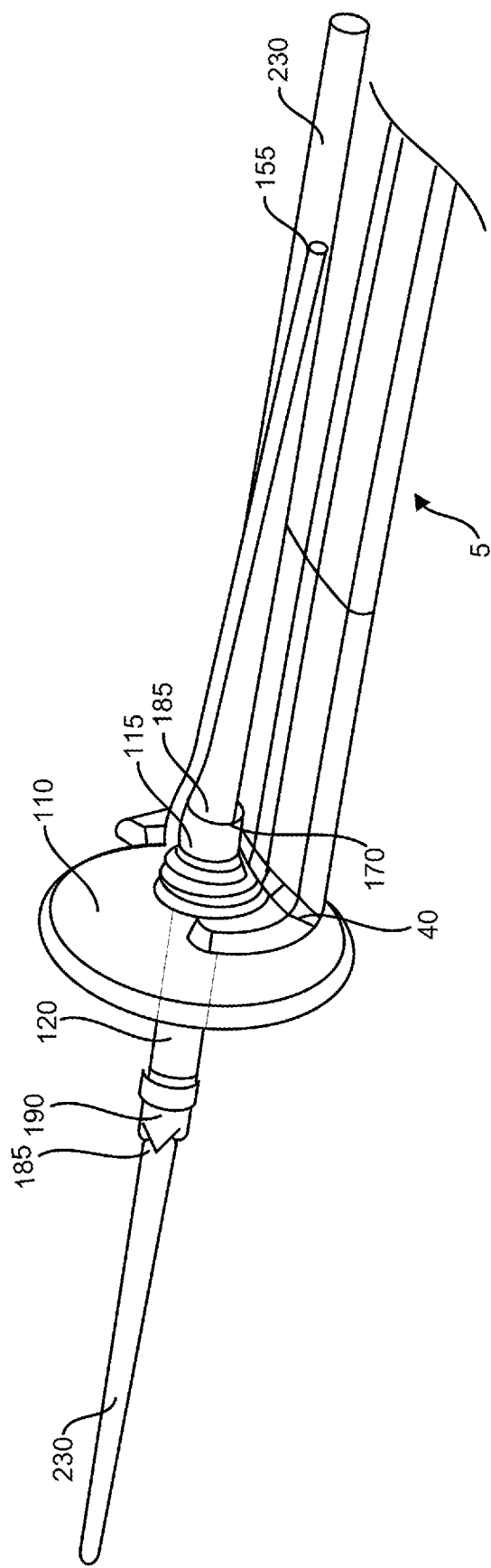
FIG. 7 is a focused perspective view of the disclosed system shown in FIG. 6.
Figure 8:
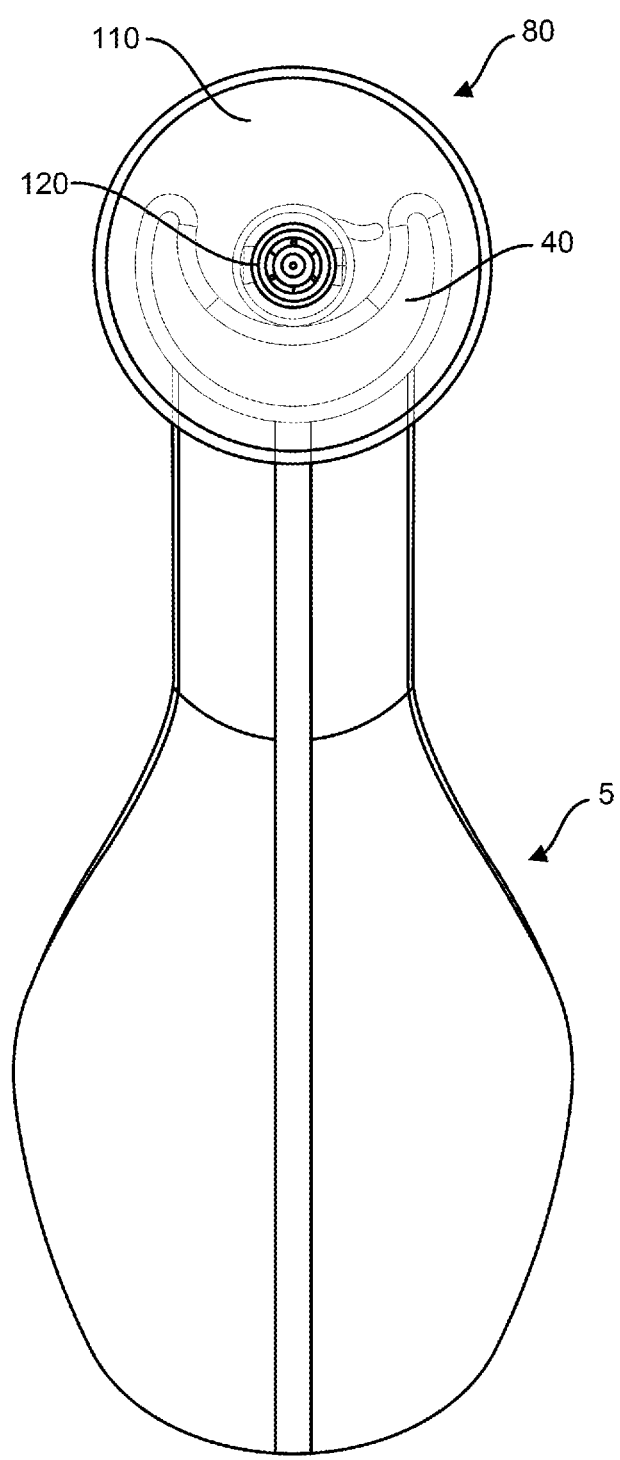
FIG. 8 is a front view of the disclosed system shown in FIG. 6 wherein the shield of the cervical plug is translucent.
Figure 9:
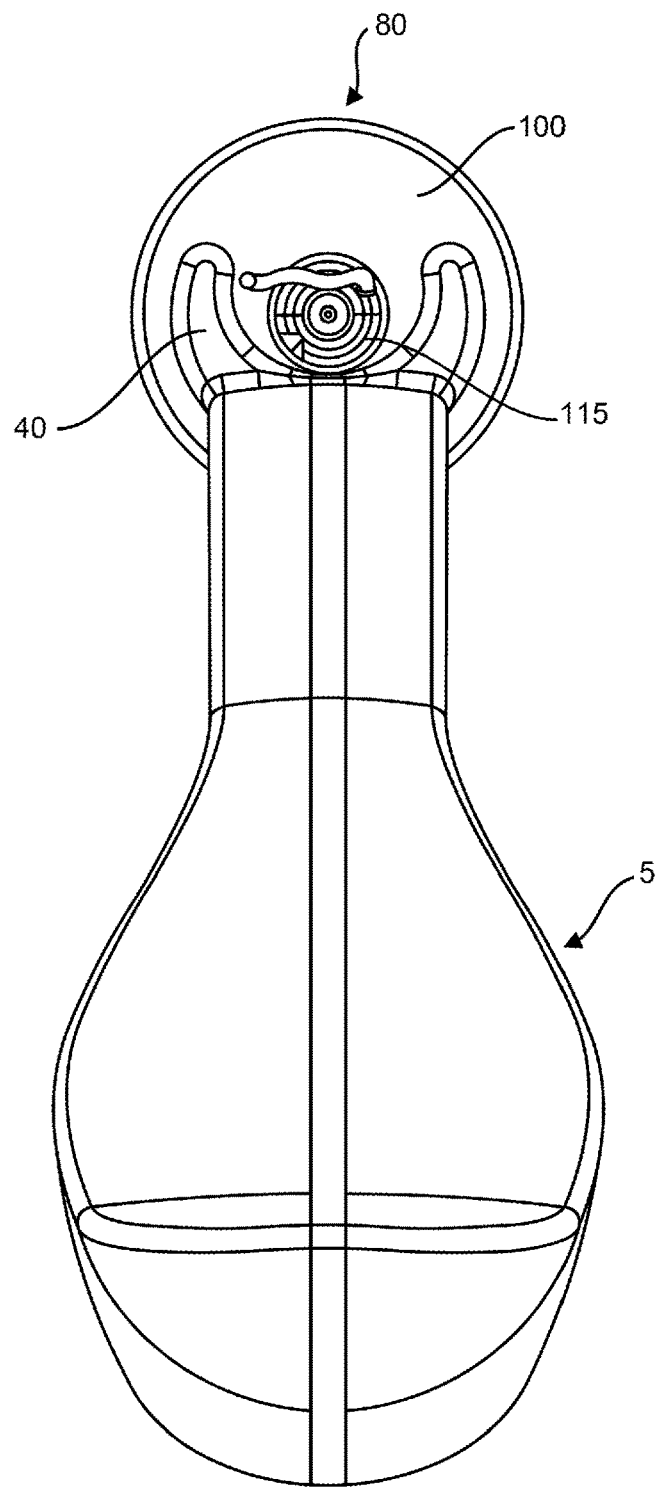
FIG. 9 is a back view of the disclosed system shown in FIG. 6.

As shown in FIG. 5, the disclosed system comprising the positioning tool 5, catheter 230, and cervical plug 80 is shown. As described more fully below, the catheter will be attached to a syringe 235 or some other device operable for injecting a semen deposit sample. FIGS. 6-9 closely demonstrate how the bracket 40 of the positioning tool 5 is operable to receive the insert member 115 and engage the second surface 110 of the shield 90 without interfering with the catheter 230 extending from the opening 185 at the proximal end 170 of the insert member 115. As discussed below, this configuration is critical to perform the disclosed artificial insemination method set forth in the ensuing paragraphs.

Figure 10:
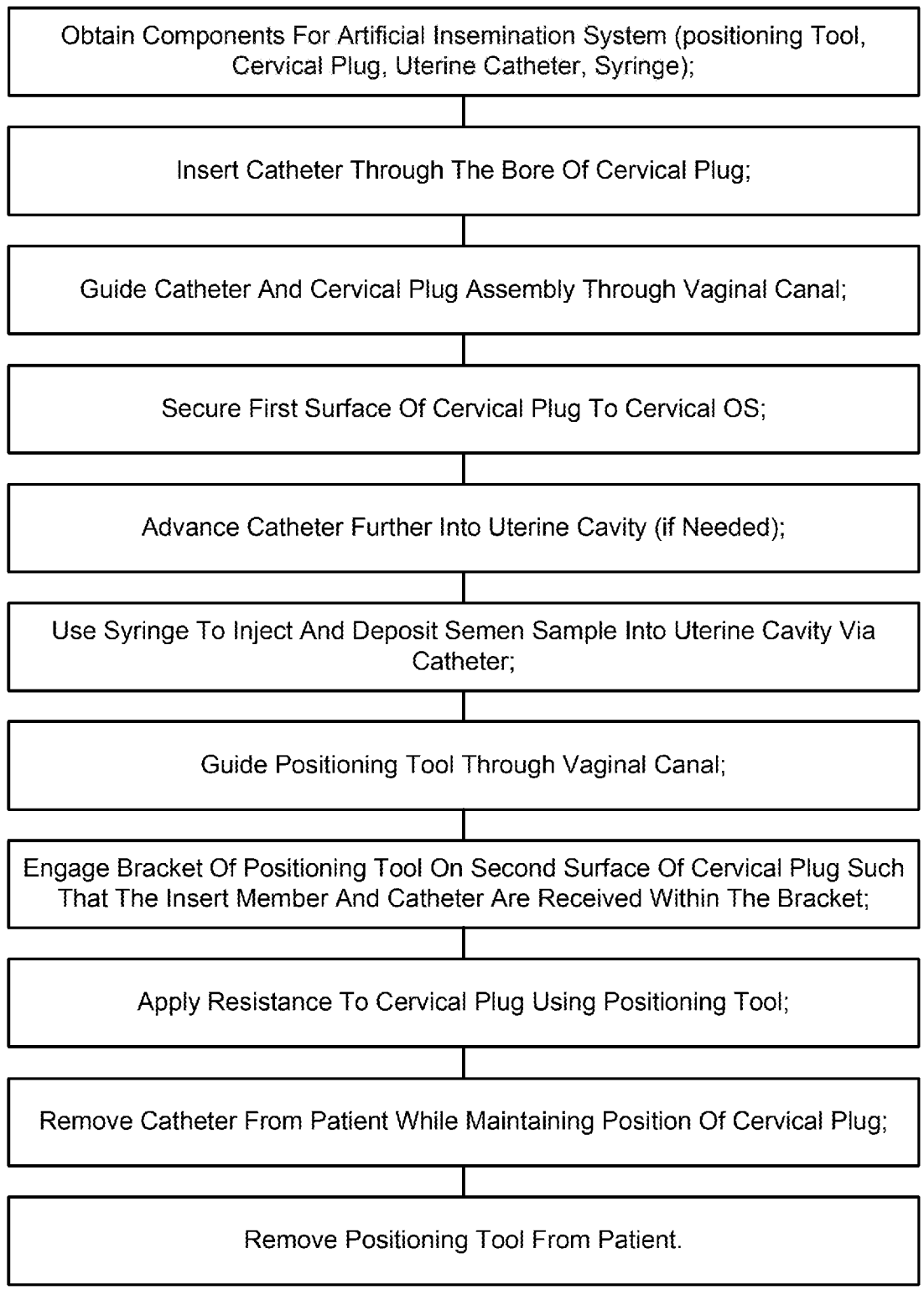
FIG. 10 is flow diagram showing the method utilizing the disclosed system.

Turning to FIG. 10, a flow diagram describing a method using the above described system of a cervical plug 80, catheter 230, and positioning tool 5, is shown. After obtaining these system components, the first step in the method requires the user to insert the catheter 230 into the opening 185 of the bore located at the proximal end 170 of the insert member 115 of the cervical plug 80. Next, the user pushes the catheter 230 through the entire length of the bore 180 until the catheter exits the other opening 185 of the bore located at the distal end 140 of the arm 120. As the catheter 230 passes through the opening 185 at the distal end 140 of the arm 120, the valve 190 opens by allowing the elastomeric flaps 220 to extend outward away from the distal end 140 of the arm 120. Depictions of the catheter 230 passing through the bore and exiting the cervical plug 80 at the distal end 140 of the arm 120 are shown in more detail in FIGS. 5-9. Although this portion of the method includes the step of inserting the catheter 230 through the cervical plug 80, it is anticipated that these two components could be preassembled with the catheter 230 already extending through the bore and the valve 190 in an open position (as shown in FIG. 4).

Whether preassembled, or combined by the user, the next step is to manually guide the catheter 230 and cervical plug 80 assembly through the vaginal canal 235 of the female patient until the first surface 100 of the shield 90 for the cervical plug 80 contacts and covers the cervical os 105, such that the arm 120 and the portion of the catheter 230 extending therefrom enter the cervical canal 240. The user then advances the catheter 230 into the uterine cavity 250. Next, a semen sample is deposited through the catheter 230, preferably using a syringe 235 or other mechanism known in the art for advancing a semen sample through a catheter 230. FIG. 11 shows the catheter 230 fully advanced into the uterine cavity 250 and the cervical plug 80 in place at the cervical os 105.

After the semen sample is deposited into the uterine cavity 250, the catheter 230 must be promptly removed as any foreign object within the uterine cavity 250 may trigger a biological response that could kill the injected semen or otherwise reduce the chances of a successful pregnancy. Accordingly, the next step is to remove the catheter 230 while leaving the cervical plug 80 in place to keep the deposited semen within the uterine cavity 250 and prevent any loss due to reflux. However, due to frictional forces between the catheter 230 and the inner surface of the bore within the cervical plug 80, the cervical plug 80 is likely to become dislodged when the catheter 230 is pulled through the bore. Accordingly, prior to removal of the catheter 230, the next step is for the user to guide the positioning tool 5 through the vaginal canal 235 until the bracket 40 of the positioning tool 5 engages the second surface 110 of the shield 90 of the cervical plug 80, such that the insert member 115 and catheter 230 are received within the opposing spaced apart segments 60 of the bracket 40. FIG. 12 shows the catheter 230 fully advanced into the uterine cavity 250, the cervical plug 80 in place at the cervical os 105, and the positioning tool 105 engaged with the cervical plug 80.

With the positioning tool 5 is in place, the next step is for the user to apply force to the second surface 110 of the shield 90 using the tool 5; the resistance created by this force is enough to counter the frictional forces generated when the catheter 230 is subsequently pulled back through the bore of the cervical plug 80 and ultimately out of the female patient. As the catheter 230 is pulled back through the opening 185 at the distal end 140 of the arm 120, the valve 190 returns to its closed position 210 (as shown in FIG. 3) by having the elastomeric flaps 220 retract and form a substantially fluid-tight seal around the distal end 140 of the arm 120. The fluid tight seal at the opening 185 in combination with the cervical plug 80 remaining in place at the cervical os 105, maximizes the retainment of the semen sample in the uterine cavity 250, thus increasing the likelihood of a successful pregnancy.

After a suitable period of time, the cervical plug 80 may be removed. The cervical plug 80 may be removed via the insert member 115 using forceps or a similar instrument. Alternatively, the cervical plug 80 may be removed by pulling the cervical plug 80 through the vaginal canal 235 via the string 155.

For the purposes of promoting and understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the system (and components of the individual operating components of the system) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical." Numerous modifications and adaptations will be readily apparent to those skilled in this art without departing from the spirit and scope of the present invention.

What is claimed is:

1. An artificial insemination system comprising:
   a cervical plug further comprising,
      a shield having a first surface and opposing second surface, wherein the shield is operable to cover an orifice;
      an arm having a proximal end secured to the first surface of the shield and a distal end operable to insert into an orifice;

an insert member having a proximal end and distal end wherein the distal end is attached to the second surface of the shield;

a bore extending longitudinally through the arm, shield, and insert member, wherein the bore has an opening at the distal end of the arm and an opening at the proximal end of the insert member; and wherein the shield and the arm are operable to secure the cervical plug in place during use;

a positioning tool further comprising, a handle having a proximal end and a distal end;

a bracket further comprising a bottom segment attached to two opposing spaced apart segments extending therefrom;

a stem portion;

wherein the stem portion connects the distal end of the handle to the bracket; and a catheter;

wherein the bore of the cervical plug is operable to receive the catheter; and wherein the bracket of the positioning tool is operable to receive the insert member of the cervical plug.

2. The artificial insemination system of claim 1 wherein the stem portion of the positioning tool curves from the bracket to the distal end of the handle.

3. The artificial insemination system of claim 1 wherein the opposing spaced apart segments of the positioning tool are linear.

4. The artificial insemination system of claim 1 wherein the opposing spaced apart segments of the positioning tool are curvilinear.

5. The artificial insemination system of claim 1 wherein the cervical plug further comprises a valve disposed at the distal end of the arm, wherein the valve is operable between an open position and a closed position, wherein the valve comprises a plurality of elastomeric flaps integrally attached to the distal end of the arm, wherein the elastomeric flaps are resiliently biased against each other when the valve is in the closed position, wherein the elastomeric flaps are each sized and shaped to for a substantially fluid-tight seal over the opening at the distal end of the arm when the valve is in the closed position.

6. The artificial insemination system of claim 1 wherein the first surface of the shield is concave.

7. The artificial insemination system of claim 1 wherein the shield of the cervical plug is translucent.

8. The artificial insemination system of claim 1 wherein the shield of the cervical plug is opaque.

9. A method for performing intrauterine insemination, said method comprising the steps of:

providing a cervical plug comprising, a shield having a first surface and opposing second surface, wherein the shield is operable to cover an orifice;

an arm having a proximal end secured to the first surface of the shield and a distal end operable to insert into an orifice;

an insert member having a proximal end and distal end wherein the distal end is attached to the second surface of the shield;

a bore extending longitudinally through the arm, shield, and insert member, wherein the bore has an opening at the distal end of the arm and an opening at the proximal end of the insert member; and wherein the shield and the arm are operable to secure the cervical plug in place during use;

providing a positioning tool comprising, a handle having a proximal end and a distal end;

a bracket further comprising a bottom segment attached to two opposing spaced apart segments extending therefrom;

a stem portion;

wherein the stem portion connects the distal end of the handle to the bracket; and wherein the bracket of the positioning tool is operable to receive the insert member of the cervical plug;

providing a catheter;

inserting the catheter into the bore through the opening on the proximal end of the insert member;

pushing the catheter through the opening at the distal end of the arm;

guiding the catheter and cervical plug through a vaginal canal of a patient until the first surface of the shield covers a cervical OS of said patient;

introducing a semen sample into a cervical canal or a uterine cavity of said patient via the catheter;

introducing the positioning tool into the cervical canal; and engaging the bracket of the positioning tool around the insert member of the cervical plug and applying resistance to the second surface of the shield while the catheter is removed.

10. The method of claim 9 further comprising the step of removing the cervical plug.

11. The method of claim 10 further comprising the step of removing the cervical plug using forceps.

12. The method of claim 10 further comprising the step of providing a string that is attached to the insert member, wherein the cervical plug is removable from the patient by pulling on the string.

13. The method of claim 9 further comprising the step of providing a valve disposed at the distal end of the arm of the cervical plug, wherein the valve is operable between an open position and a closed position, wherein the valve comprises a plurality of elastomeric flaps integrally attached to the distal end of the arm, wherein the elastomeric flaps are resiliently biased against each other when the valve is in the closed position, wherein the elastomeric flaps are each sized and shaped to form a substantially fluid-tight seal over the opening at the distal end of the arm when the valve is in the closed position.

* * * * *